United States Patent [19]

Cavitt

[11] 4,374,260

[45] Feb. 15, 1983

[54] ETHYLENE OXIDE PRODUCTION

[75] Inventor: Stanley B. Cavitt, Austin, Tex.

[73] Assignee: Texaco Inc., White Plains, N.Y.

[21] Appl. No.: 391,651

[22] Filed: Jun. 24, 1982

Related U.S. Application Data

[63] Continuation-in-part of Ser. No. 893,726, Apr. 5, 1978, abandoned, which is a continuation-in-part of Ser. No. 719,042, Aug. 30, 1976, Pat. No. 4,097,414.

[51] Int. Cl.$^3$ .......................................... C07D 301/10
[52] U.S. Cl. ..................................... 549/534; 252/476
[58] Field of Search .......................................... 549/534

[56] References Cited

U.S. PATENT DOCUMENTS

| | | | |
|---|---|---|---|
| 3,956,184 | 5/1976 | Kruglikov et al. | 252/476 |
| 3,962,136 | 6/1976 | Nielsen et al. | 549/534 |
| 4,007,135 | 2/1977 | Hayden et al. | 252/467 |
| 4,012,425 | 3/1977 | Nielsen et al. | 549/534 |

*Primary Examiner*—Norma S. Milestone
*Attorney, Agent, or Firm*—Robert A. Kulason; Jack H. Park; Kenneth R. Priem

[57] ABSTRACT

An improved method is disclosed for the vapor phase epoxidation of ethylene to ethylene oxide which includes intimately contacting an ethylene-containing feed stream with an epoxidizing amount of molecular oxygen epoxidizing agent in the presence of a catalytically effective amount of an improved catalyst comprising an inorganic porous support containing metallic silver and an effective amount of a cesium promoter which have been deposited coincidentally on the support, and, optionally, an effective amount of at least one inhibitor which retards combustion of ethylene to carbon dioxide at temperatures of from about 200° C. to about 300° C.

The novel silver catalyst is best described in terms of its method of preparation. The catalyst is prepared by impregnating certain inorganic porous substrates with a specific silver carboxylate/amine complex, such as silver oxalate/diethylenetriamine complex, impregnating solution containing an effective amount of a cesium salt. The impregnated support is then heated in order to evaporate volatiles, decompose the complex and activate the catalyst.

15 Claims, No Drawings

ETHYLENE OXIDE PRODUCTION

This application is a continuation-in-part of application Ser. No. 893,726, filed Apr. 5, 1978, now abandoned, which is a continuation-in-part of application Ser. No. 719,042, filed Aug. 30, 1976, now U.S. Pat. No. 4,097,414, issued June 27, 1978.

BACKGROUND OF THE INVENTION

1. Field of the Invention

This invention relates to vapor phase epoxidation reactions of ethylene with molecular oxygen; and, more particularly to epoxidation reactions using specific cesium-promoted silver catalysts.

2. Description of the Prior Art

The preparation of ethylene oxide by the oxidation of ethylene in the presence of suitable catalysts is well known. These known processes can be generally separated into two groups; the first utilizes air and the second utilizes molecular oxygen, e.g., from about 85 mol percent to about 99 mol percent. "Silver catalysts" are utilized with both groups.

Although the first reference to the use of silver as such a catalyst was made by Walter in British Pat. No. 21,941 (1905), it was not until some thirty years later that the first disclosures were made of the use of silver as a catalyst in the vapor phase oxidation of ethylene to ethylene oxide. See Societe Francaise de Catalyse Generalisee, French Pat. No. 729,952 (1932); and Lefort, U.S. Pat. No. 1,998,878 (1935).

Since silver is expensive, optimizing the amount of silver employed in a supported catalyst for a desired conversion and selectivity to products has been widely investigated. A variety of techniques have been developed for the depositing of relatively small, but highly active amounts of silver on surfaces of non-silver supports such as alumina. For example, McKim and Cambron in *Canadian Journal of Research*, Volume 27, Section B (1949), pp. 813-827, described a method for depositing particulate silver on a support by decomposing silver oxalate in aqueous ethanolamine at 60° C. and forming a paste which is applied to the surface of the support. In U.S. Pat. No. 3,043,854 issued July 10, 1962 to Endler, a silver coating formed by decomposition of a silver carbonate slurry is applied to a catalyst support surface.

Recently it has been disclosed that supported silver catalysts can be prepared by impregnating a porous substrate with certain silver containing solutions and evaporating or decomposing the solutions to deposit silver on the substrate. U.S. Pat. No. 3,702,259 to Nielsen describes the use of an aqueous silver oxalate impregnating solution which employes a solubilizing/reducing agent of ethylenediamine, a mixture of ethylenediamine or ethanolamine and ammonia, or a mixture of ethylenediamine and ethanolamine. Van Bylandtlaan, in Belgium Pat. No. 808,278 (1974) employs an aqueous solution of hexamethylenetetramine with an ethylenediamine silver complex to deposit silver on an alumina support by decomposition. Additionally, it has been disclosed in Japanese Pat. No. 71/19,606 to Fujii et al that impregnation of inorganic supports with aqueous silver nitrate/alkanolamine complexes with subsequent thermal decomposition gives supported silver catalysts for ethylene epoxidation.

Recently it has been disclosed in British Pat. No. 1,413,251 to Nielsen and La Rochelle that certain alkali metals, such as cesium, can be deposited on a refractory support coincidentally with the silver metal (U.S. Pat. No. 3,962,136).

Surprisingly, it has now been discovered that certain cesium-promoted silver catalysts are extremely stable, physically durable and more selective in specific ethylene oxidation processes than heretofore known promoted catalysts.

The promoted silver catalyst is easily prepared by impregnating a porous, inorganic substrate with an impregnating solution comprising a solvent, a silver carboxylate, certain amines and a salt of cesium. The impregnated support is heated to decompose the complex thus depositing the silver on the substrate and activating the catalyst.

It has been found that the instant promoted catalysts provide outstanding selectivity in air oxidation processes or oxygen processes using nitrogen or other inert gas ballast. This is particularly important in that such air processes are not closed systems and some proportion of the unreacted ethylene is lost by venting excess gas. Additionally, the instant catalysts show high attrition resistance and surprisingly high mechanical strength.

SUMMARY OF THE INVENTION

According to the broad aspect of the invention, ethylene is epoxidized to ethylene oxide substantially in the vapor phase by intimately contacting ethylene with an epoxidizing amount of molecular oxygen in the presence of a catalytically effective amount of an activated, cesium-promoted, silver-containing catalyst and, optionally, with an effective amount of at least one inhibitor which retards combustion of ethylene to carbon dioxide at temperatures of from about 200° C. to about 300° C.

The cesium-modified silver catalyst comprises a porous, inorganic support containing from about 5 ppm to about 400 ppm cesium together with elemental silver. The cesium and the silver are simultaneously deposited on the support by impregnating the support with a liquid phase comprising an effective amount of a cesium cation dispersed in a silver carboxylate/amine complex. The impregnated support is then heated at temperatures of from 50° C. to 300° C. to evaporate volatiles, decompose the complex, and activate the catalyst.

The complex is formed by dissolving a silver carboxylate in an amine-containing complexing agent comprising diethylenetriamine.

DESCRIPTION OF THE PREFERRED EMBODIMENTS

In accordance with a preferred embodiment, ethylene is epoxidized to ethylene oxide in a continuous process by contacting a feed material which comprises from about 5 mol percent to about 20 mol percent ethylene, from about 5 mol percent to about 10 mol percent oxygen, from about 4 mol percent to about 12 mol percent carbon dioxide, trace amounts of a suitable inhibitor and the remainder nitrogen. Another preferred composition would be 20 to 60 mol percent methane, 15 to 30 mol percent ethylene, 7 to 10 mol percent oxygen, 4 to 12 mol percent carbon dioxide and the remainder nitrogen. The feed stream in vapor phase is contacted with a catalytically effective amount of a specific activated, supported, cesium-modified, silver-containing catalyst, at temperatures from about 220° C. to about 260° C. and at pressures in the range of from about 13 atm. to about 20 atm.

The cesium-promoted silver catalyst of the instant invention has been shown to be a particularly selective catalyst in the direct oxidation of ethylene with molecular oxygen to ethylene oxide. The epoxidation of ethylene to ethylene oxide can best be described as a controlled oxidation. It is important to minimize complete oxidation in accordance with the epoxidation process while maximizing the selectivity and conversion to the desired epoxidized products.

The conditions for carrying out such an oxidation reaction in the presence of silver catalyst generally and more particularly the novel, promoted catalyst of the instant invention are broadly described in the prior art. Such methods and manner of production are well known to the skilled artisan. For example, those methods which appear and are described in U.S. Pat. No. 3,119,837, British Pat. Nos. 1,314,613 and 1,132,095. These teachings apply to a number of conditions including suitable temperatures, pressures, residence times, diluents, inhibitors and the like. Additionally, the desirability of recycling unreacted feed or use of successive conversion processes such as by employing series reactors can be readily determined by the skilled artisan.

It has been found that the promoted silver catalyst of the instant invention is surprisingly stable under a broad spectrum of reaction conditions, while maintaining a high degree of selectivity and productivity.

Regardless of the character of the support utilized, the catalyst is preferably shaped into particles, pellets, spheres or the like of a suitable size for employment in fixed bed application. It will be realized that conventional commercial fixed-bed ethylene oxidation reactors may be utilized. Such reactors typically take the form of a plurality of parallel, elongated tubes packed with a catalyst material.

Generally it has been found that the promoted catalyst of the instant invention is useful for so-called air oxidation process or oxygen processes wherein ballast "gases" are primarily comprises of nitrogen, argon or helium as well as the hydrocarbon type component such as methane, ethane or large excesses of ethylene. Surprisingly, it has been known in such processes (as will be seen in the following examples) that the promoted catalyst of the instant invention shows an unexpected improvement over prior art unpromoted catalysts.

Generally, the process is carried out in vapor phase wherein a single gaseous feed stream is continuously charged to a suitable catalyst-containing reactor. The reaction is carried out at temperatures from about 200° C. to about 300° C., and preferably in the range of about 220° C. to about 260° C. The pressures are not critical and may vary from about atmospheric to about 35 atm. with about 13 atm. to about 20 atm. being preferred at the preferred temperature range. The feed admixture is preferably fed in a single stream to the reactor in order that the constituents be thoroughly admixed.

The complex is formed by dissolving a silver carboxylate in an amine-containing complexing agent comprising the polyalkylene polyamine diethylenetriamine.

The supported cesium-promoted silver catalyst of the instant invention is prepared in four steps. In a first step, an impregnating solution comprising a solvent, a salt of cesium, and a silver carboxylate/amine complex, as more fully described hereinafter, is prepared by dissolving a silver carboxylate in an excess of a polyalkylene polyamine having terminal primary nitrogen moieties at temperatures sufficient to dissolve the silver carboxylate to form the silver carboxylate/amine complex. To the formed complex is added a solution of a salt of cesium dissolved in the solvent.

In a second step, an inorganic porous support, as more fully described hereinafter, and preferably a high-purity α-alumina support, is impregnated by immersing the support in the impregnating solution at about atmospheric pressure and then subjecting the immersed support to vacuum at temperatures of from about 20° C. to about 40° C. After the vacuum is broken, the excess solution is drained. In a third step, the drained support is heated to evaporate volatiles at temperatures of from about 50° C. to 150° C. in a forced-air heater for a time from about 1 to about 12 hours. In a final step, the dried, impregnated support is heated in the presence of forced air at temperatures of from about 200° C. to about 300° C. to decompose the silver carboxylate/amine complex and activate the supported, promoted silver catalyst material.

The Impregnating Solution

The impregnating solution of the instant invention comprises a salt of cesium and a silver carboxylate/amine complex. The impregnating solution can best be characterized as a homogeneous liquid at impregnating temperatures. The silver carboxylate/amine complex is formed by dissolving a silver salt of an organic acid in a certain amine-containing complexing agent. Surprisingly, these silver carboxylate/amine complexes are stable in high solution concentrations at impregnating temperatures, and contain large amounts of silver which are carried to the support. Additionally, these complexes yield a solution which is compatible with most cesium salts and are of a viscosity which is suitable for impregnation of porous, inorganic supports.

The silver carboxylate/amine complex-containing impregnating solutions of the instant invention can best be described in terms of their method of preparation. Specifically, a silver salt of an organic acid is dissolved in a certain amine-containing complexing agent at temperatures in the range of from about 0° to about 50° C.

The useful silver salts of organic acids can be generally described as silver carboxylates which readily thermally decompose. Such compounds can be carboxylates of mono-carboxylic or poly-carboxylic acids. Preferably, the silver salt is of a mono-carboxylic or di-carboxylic acid, wherein the organic moiety contains less than about 10 carbon atoms. Those carboxylates of less than about 10 carbon atoms are preferred in order to obtain a favorable concentration of silver in the organic acid salt, and ultimately thus in the complex solution, while providing for facile thermal decomposition. It should be noted that while silver salts of organic acids containing more than about 10 carbon atoms are useful, they produce a silver/amine complex which becomes increasingly difficult to decompose as the molecular weight increases and will reduce the amount of silver ultimately available for deposition on the support.

Examples of suitable silver carboxylates include silver carbonate, silver acetate, silver malonate, silver glycolate, silver oxalate, silver formate, silver citrate, silver lactate, silver pyruvate, and the like. The most preferred silver carboxylates are silver oxalate and silver acetate because of availability and solubility.

The useful amine-containing complexing agent of the instant invention is the polyalkylene polyamine diethylenetriamine.

The amount of diethylenetriamine utilized in forming the silver carboxylate/amine complex impregnating solution is somewhat empirical. Generally that amount of amine complexing agent sufficient to completely dissolve the silver salts is utilized. Normally, this amount will be a slight molar excess of the amine containing agent. This amount can be readily determined by the skilled artisan in that it is generally that amount sufficient to completely dissolve the required amount of silver salt, which can be determined by observation. The amount of silver salt required is somewhat empirical and generally determined by the amount of silver ion required in solution and the porosity of the support.

As hereinbefore mentioned, it is desirable to have the complex as "rich" as possible in silver. Generally, the impregnating solution should contain an amount of about twice that desired in the finished catalyst on a weight percent basis with a support having a 50% porosity. It is preferable, therefore, to obtain a complex which contains more than about 10 weight percent silver in the impregnating solution and more preferably from about 12 to about 25 weight percent silver.

It is desirable to have from about 1 to about 6 amine equivalents of diethylenetriamine for each equivalent of silver in order to form the optimum complex containing solution.

The silver salt is preferably dissolved in the amine containing agent at temperatures in the range of about 20° C. to about 40° C. Temperatures in excess of 50° C. are not preferred, since higher temperatures tend to cause accelerated decomposition of the complex.

If desired, solubilizers can be added in order to facilitate dissolution of the silver salt in the amine complexing agent. Examples of such solubilizers include water, aqueous ammonia, and the like. In accordance with a preferred embodiment, water is utilized as the solubilizing agent. Water not only reduces the viscosity of the impregnating solution, the amount of amine required to solubilize the silver salt, and potential hazards of handling the solution, but also acts as a solvent for the silver salt/amine complex, as well as the cesium salt thus preventing premature precipitation.

Examples of suitable solubilizers include aqueous methylamine, ethylamine, diethylamine, triethylamine, and pyridine. It is, however, recognized that the marginal advantages of such solubilizers may be outweighed by the fact that certain lower molecular weight amines or ammonia can form explosive solids with silver. In addition, although not necessary, small amounts of hydrogen peroxide or other suitable oxidizing agents may be added to minimize premature reduction of the silver in the complex.

The cesium metal salts which can be utilized are generally those which are soluble in the silver/amine complex. The metal is deposited on the surface of the support in the form of the cation rather than the free alkali metal. For example, as nitrates, nitrites, hydroxides, carbonates, bicarbonates, oxalates, acetates, tartrates, lactates, perchlorate and the like. It should be noted, however, that those cesium metal salts which react with or cause the silver present in the amine complex to precipitate prematurely should be avoided. A cesium salt of an organic carboxylic acid or cesium hydroxide is conveniently used. Cesium hydroxide is preferred.

The amount of the cesium metal salt present in the impregnating solution will depend upon that amount desired in the activated catalyst, the solubility of the salt, the stability of the complex, the porosity of the support, etc. Generally that amount of cesium salt sufficient to deposit from about $4 \times 10^{-5}$ gew to about $3 \times 10^{-3}$ gew cesium per kilogram of finished catalyst is effective. Suitable impregnating solutions contain from about 10 ppm to about 600 ppm cesium cation. The amount of cesium cation required in solution is capable of determination by conventional analysis of the amount of material actually deposited. Generally, the impregnating solution should contain an amount about twice that desired in the finished catalyst on a ppm basis with a support having about 50% porosity.

The Support

The support utilized to form the novel promoted silver catalyst of the instant invention can be generally described as a porous, inorganic substrate having those characteristics which are well known in the art and particularly known in the ethylene epoxidation art. Suitable supports which can be used in accordance with the instant invention are glass, alumina, silica, silica-alumina, inert metals, silicon carbide and zirconia. It is essential that the support chosen have a high porosity (i.e., high solvent absorption), low surface area and a controlled pore size. Preferably, from about 70% to 100% of the pore diameters are between about 1 and $30\mu$ and more preferably between about 1 and about $10\mu$. The advantages of the instant catalyst are paticularly evident when $\alpha$-alumina supports are utilized. The useful support particles would have minimum external dimensions of about 6 mm and a maximum of about 13 mm.

A preferred support media has an average pore diameter of from about 3 to about $7\mu$ with a pore volume of from about 0.3 to about 0.6 cc/g and has a surface area less than about 1 m$^2$/g. A particularly preferred support is high purity $\alpha$-alumina having the above characteristics.

Preparation of the Supported Silver Catalyst

In preparing the stable, promoted silver catalyst of the instant invention, a suitable support is first contacted with the impregnating solution and subsequently heated at elevated temperature to first evaporate the volatiles and finally to decompose the silver carboxylate/amine complex and activate the catalyst material. Although the preparation of the supported catalyst can be accomplished in two steps; i.e., an immersion step and an evaporation, activating, and decomposition step at incrementally increasingly elevated temperatures, it is preferable to prepare the catalyst of the instant invention in three distinct steps.

After the impregnating solution has been prepared as described hereinabove, the substrate to be impregnated is contacted with the solution in a first step. This is preferably accomplished by immersion of the substrate in a suitably large body of impregnating solution to completely cover the substrate. The immersed substrate is then subjected to an evacuated atmosphere for a time period sufficient to remove entrapped air from the support pores at temperatures of from about 0° C. to about 50° C. and more preferably from about 20° C. to about 40° C.

The impregnation time will depend on the characteristics of the substrate and the viscosity of the impregnating solution and can be readily determined by the skilled artisan. Although somewhat empirical, it is generally sufficient to contact the porous substrate with the impregnating solution for a time from about five minutes to several hours. When utilizing impregnating solutions containing silver salts of polyalkylene polyamines, a time from about ten minutes to two hours is sufficient. After the substrate has been contacted for sufficient time under vacuum, the vacuum is broken to return the pressure to atmosphere and then the excess solution is physically drained from the substrate.

In a second stage the drained substrate is dried in the presence of a heated, flowing gas stream. The stream may comprise air or air diluted with sufficient inert gas to render the admixture substantially inert. The gas stream is heated to temperatures of from about 50° C. to 150° C. for a period sufficient to evaporate the volatiles. Generally the time required to dry the impregnated substrate is somewhat empirical and can be readily determined by the skilled artisan for a particular substrate and impregnating solution. Time periods of from about one to about twelve hours have been found sufficient. It should be noted that, during the drying step, temperatures in excess of about 150° C. should be avoided as the complex may tend to decompose too rapidly and/or cause the volatiles to evaporate so readily as to disturb the uniformity of the catalyst material. Although not required, it is found that first thoroughly drying the impregnated substrate prior to thermal decomposition yields a more uniform catalyst.

In the third step the dried impregnated substrate is heated in the presence of flowing air, or a flowing inert atmosphere to temperatures in excess of about 180° C. and preferably from about 200° C. to about 300° C. to decompose the complexing agent and activate the supported silver catalyst materials. The time required to thoroughly decompose the silver salt/amine complex and activate the catalyst is somewhat empirical but generally times in the range from about one to twelve hours have been found sufficient.

It will be realized by the skilled artisan that when other solvents such as water, or aqueous solubilzing agents such as aqueous ammonia, aqueous alkylamines, and the like are present in the complexing agent, the times required for drying may be somewhat variable. The specific times required are generally within the above broad limits and can be determined by the skilled artisan without undue experimentation. Additionally, when high molecular weight amines are utilized, washing of the dried substrate may be advantageous to remove excess organic material prior to activation. The washing may be accomplished in a conventional manner with lower alkanols.

The invention will be further illustrated by the following specific examples, which are given by way of illustration and not as limitations on the scope of this invention.

EXAMPLE I

This example illustrates preparation of the stable, supported silver catalyst of the instant invention. In a first step, silver oxalate was prepared. To an appropriate clean, dry vessel equipped with stirring apparatus were charged a solution of 18.4 g potassium oxalate dissolved in 150 cc deionized water and a solution of 34.0 g silver nitrate in 150 cc deionized water. The two solutions were admixed at 60° C. and atmospheric pressure by stirring for several minutes. The mixture was then filtered and the residue washed with four aliquots of hot, deionized water totaling 50 cc. The residue was then further washed with two 25 cc aliquots of absolute methanol. The residue was then partially air dried by evacuating the lower portion of the filter surface.

In a second step, the slightly moist filter cake was slurried in 30 ml deionized water. A solution of 0.066 g of 50% aqueous cesium hydroxide was added, followed by a mixture of 30 g diethylenetriamine and 10 g deionized water. The latter was added slowly with stirring to prevent overheating. The resulting solution was dark and contained traces of suspended solids.

In a third step, the solution prepared in step two was used as an impregnating solution. The solution was drawn into a 500 ml stainless steel sampling cylinder containing 50 g of an alumina support having a pore volume of 0.41 cc/g, a surface area of less than about 1 m$^2$/g and an average pore diameter of 5.9$\mu$. Full pump vacuum was maintained on the cylinder for about one hour. The cylinder was returned to atmospheric pressure, and allowed to stand about 10 minutes. The cylinder was then subjected to 200 psig nitrogen pressure for about 30 minutes to assure that the support pores were completely filled with impregnating solution. The excess solution was then drained from the support and the cylinder purged with nitrogen several times.

In a fourth step, the cylinder was attached to a forced-air heater and dried for one hour at 120°±5° C., then raised to about 250° C. This temperature was maintained after one hour using a 50 scfm stream of air at 40 psig. After cooling, the catalyst material weighed 56 g and contained 12.2 wt percent silver. The estimated cesium concentration on the catalyst was in the range of 130–180 ppm based on the total weight of the catalyst.

EXAMPLE II

This example illustrates the preparation of a nonpromoted silver catalyst. In a first step a silver oxalate was prepared by admixing 102 g of reagent grade silver nitrate and 44 g of reagent grade ammonium oxalate. The admixture was filtered and washed, first with small portions of hot water, then with small portions of anhydrous methanol. The residue was aspirated nearly dry under vacuum.

In a second step, the moist silver oxalate was added to a beaker containing 110 ml of deionized water, then stirred to form a slurry. The slurry was then chilled below room temperature. Keeping the solution below 60° C., a solution containing 90 g diethylenetriamine (DETA) and 30 ml deionized water was slowly added. The resulting solution was dark brown and contained traces of suspended black solids.

In a third step the support was impregnated with the impregnating solution prepared in step two. About 325 g of low surface area, high porosity, $\alpha$-alumina support of controlled pore size was immersed in the impregnating solution. The immersed support was then subjected to vacuum for 10 minutes and then returned to atmospheric pressure for 30 minutes.

In a fourth step, the impregnated support was drained, then placed in a forced air dryer and heated at about 125° C. in a rapid stream of dry air for one hour. The support was then heated to about 250° C. over a period of about one hour and held at that temperature for one hour.

The catalyst material weighted 359 g and contained 9.7 weight percent silver by atomic absorption analysis.

EXAMPLE III

In this example a cesium promoted catalyst was prepared, using the procedures and apparatus of Example II. Prior to the formation of silver oxalate slurry, as described in the second step of Example II, 0.23 g of 50% aqueous CsOH solution was added to the deionized water. The amount of support material impregnated in accordance with the procedure as described in step three of Example II was 280 g.

The prepared catalyst material showed 10.0 weight percent silver by atomic absorption.

EXAMPLE IV

In this example, a cesium-promoted catalyst was prepared. In a first step, 150 g of reagent grade ammonium oxalate and 340 g of reagent grade silver nitrate were admixed in solution, then washed and dried essentially by the manner of Example II. The silver oxalate slurry was stirred for 30 minutes, then filtered under aspirator vacuum. The residue was washed first with 400 ml of hot, deionized water in small portions, then with small portions of anhydrous methanol, using a total of 400 ml of methanol. The solid was then aspirated nearly dry under vacuum.

In the second step, the silver oxalate was slurried in a solution of 0.66 g of 50% aqueous cesium hydroxide in 300 ml deionized water. The slurry was stirred with cooling in an ice bath. A cold solution of 300 g DETA and 100 g deionized water was then added to the slurry with stirring, and the resultant admixture maintained at about 35° C. The solids of the slurry dissolved to give 1041 g of a dark solution containing traces of suspended, very fine black solids.

In the third step, a high porosity α-alumina support which had been previously screened to pass a ¼ inch mesh screen but was retained on a No. 3½ ASTM sieve was impregnated. The support was immersed in the solution at atmospheric pressure and then evacuated to about 1 mm Hg for a few minutes, and again allowed to attain atmospheric pressure.

In the fourth step, the immersed material was allowed to stand at atmospheric pressure and then the liquid was decanted. The wet solids were placed on 14"×16" stainless steel trays which in turn were placed in a forced air production oven. Employing maximum intake and exhaust settings with no recirculation, the material was heated at 120° C. for 2 hours. The temperature was then increased to 250° C. for one hour at 25% fresh air intake, 75% recycle. The oven was then cooled to 50° C. with a one-pass air stream.

The prepared catalyst material weighed 1880 g. The material was divided into two separate samples and analyzed by atomic absorption. The analysis showed 10.2 and 10.0 weight percent silver.

EXAMPLE V

An unpromoted silver catalyst was then prepared using the procedure, apparatus and reactants of Experiment IV except that the cesium hydroxide was eliminated in step two.

EXAMPLE VI

In this example the promoted catalyst prepared in Example I was compared with a nearly identical unpromoted catalyst. The difference in preparation between the two resides in the absence of the 0.066 g 50% aqueous cesium hydroxide which was added in step two of Example I. For the comparison, a miniature ethylene oxide reactor was employed utilizing 3.5 g of 30-40 mesh catalyst in a 0.2×5" reaction zone. The test was run at a reactor temperature of 220° to 250° C., mass velocity of about 5 g feed/g of catalyst per hour, and reactor pressure of 200 psig. The feed gas composition was 7 percent ethylene (99.8 mol % minimum purity), 6 percent oxygen and the balance nitrogen. The performance results at comparable ethylene conversions are shown in Table I at different reactor temperatures. Ethylene dichloride inhibitor was added in amounts necessary to optimize selectivity.

TABLE I

| Run No. | Temp. | Promoted Selec. | Promoted Conv. | Unpromoted Selec. | Unpromoted Conv. |
|---|---|---|---|---|---|
| 1 | 220° C. | 77 | 28 | 78 | 28 |
| 2 | 230° C. | 76 | 36 | 75 | 35 |
| 3 | 240° C. | 75 | 45 | 73 | 43 |
| 4 | 250° C. | 75 | 52 | 68 | 50 |

This example demonstrates that the promoted catalyst gives higher selectivities under reaction conditions wherein the conversion rates are most favorable.

EXAMPLE VII

In this example the catalysts in Examples II and III were performance tested as in Example VI. Included for comparison are standard nonpromoted catalysts used in a commercial ethylene oxide process plant. In each run, the reactor operating conditions were adjusted so that the conversions and ethylene oxide outlet conversions and ethylene oxide outlet concentrations matched those for a typical commercial catalyst in a large pilot plant reactor. As before, ethylene feed concentration was 7 mol percent, and oxygen 6 mol percent. The $CO_2$ and ethane levels were 8 percent and 200-300 ppm, respectively, whereas in Example VI these constituents were negligible. The results are shown in Table II.

TABLE II

|  | Silver Plant Catalyst | | Promoted Catalyst Ex. III | Unpromoted Catalyst Ex. II |
|---|---|---|---|---|
|  | A | B | | |
| Temp., °C. | 260 | 257 | 251 | 244 |
| Selectivity | 70.5 | 70.3 | 77.7 | 71.2 |

As can be seen, the unpromoted catalyst of Example II showed superior activity to the plant catalyst and the promoted catalyst of the instant invention showed a marked increase in selectivity over the unpromoted catalyst material.

EXAMPLE VIII

This example shows selectivity enhancement of the promoted catalysts is related to the ingredients used in the preparation of the catalyst material. The following experiments were performed in an ethylene oxide reactor as described in Example VI at constant reactor productivity and constant conversion. All catalysts contained essentially the same amounts of silver and all promoted catalysts essentially the same amount of cesium.

TABLE III

| Run No. | Amine[1] | Promoted Selectivity | Unpromoted Selectivity |
|---|---|---|---|
| 1 | DETA[2] | 79.0 | 71.4 |
| 2 | DETA—Morpholine | 76.8 | 72.3 |
| 3 | EDA—MEA[3] | 74.4 | 72.2 |

TABLE III-continued

| Run No. | Amine[1] | Promoted Selectivity | Unpromoted Selectivity |
|---|---|---|---|
| 4 | MEA—NH$_3$ | 76.8 | 74.2 |

[1]Amine used in impregnating solution in preparation of catalyst substantially as in Example I.
[2]Diethylenetriamine
[3]Ethylenediamine-Monoethanolamine - prior art catalyst.
[4]Monoethanolamine-ammonia - prior art catalyst.

This example shows the degree of selectivity enhancement obtained using a cesium promoter is effected by the specific amines used to make the silver impregnating solution. The preferred catalyst of the instant invention prepared from a silver-DETA complex showed the greatest selectivity enhancement when a promoter was used even though it had the lowest unpromoted selectivity. Based on unpromoted selectivity MEA-HH$_3$ would have been expected to give the highest promoted selectivity.

EXAMPLE IX

In this example a catalyst was prepared from a silver-DETA complex in a manner substantially similar to that of Example I. In each preparation, the amount of cesium promoter employed was varied. Each catalyst was then employed in an epoxidation reaction wherein a constant ethylene oxide concentration in the reactor effluent was maintained. The feed stream for each run comprised about 7 mol percent ethylene, 7 to 8 mol percent CO$_2$ and 6 mol percent oxygen with promoter and inhibitor concentrations selected to provide maximum selectivity. The reactor system was substantially that described in Example VI. The results are shown in Table IV.

TABLE IV

| Run No. | Cesium conc., ppm on total catalyst | Reactor temp., °C. | Selectivity mol % |
|---|---|---|---|
| 1 | 0 | 240 | 72.0 |
| 2 | 12 | 240 | 73.8 |
| 3 | 29 | 240 | 74.9 |
| 4 | 41 | 240 | 76.2 |
| 5 | 111 | 247 | 78.1 |
| 6 | 122 | 250 | 79.0 |
| 7 | 162 | 253 | 77.7 |
| 8 | 190 | 257 | 78.2 |

While the invention has been explained in relation to its preferred embodiment, it is to be understood that various modifications thereof will become apparent to those skilled in the art upon reading the specification and is intended to cover such modifications as fall within the scope of the appended claims.

EXAMPLE X

This example compares triethylenetetramine-based catalyst prepared by reduction with formaldehyde as disclosed in U.S. Pat. No. 3,956,184 with my catalyst based on diethylenetriamine reduced thermally.

Catalysts A through G were crushed after impregnation since, in general, catalysts prepared by good impregnation techniques have similar activities for internal and external surfaces. Tests H and I represent direct comparisons of whole pellets with the catalyst being prepared according to the method of U.S. Pat. No. 3,956,184 in Run I, and the catalyst prepared by my method in Run H. These tests H and I demonstrate clearly that the external surface of catalysts prepared according to my method is superior to the catalyst prepared according to the method in U.S. Pat. No. 3,956,184. In U.S. Pat. No. 3,965,184, the catalyst was tested as manufactured as in H and I. Our tests A through G do not represent tests as performed in the '184 patent.

TABLE I

EO CATALYST TESTS - METHANE BALLAST OXYGEN PROCESS
($\Delta$EO = 1.9 mol %)

| Catalyst | Ag, wt % | Cs, ppm | Amine in Complex | Activation method | Startup temp, °C. | Time to initiation, hours | Time to max. EO, hours | T$_R$, °C. | S$_2$ | S$_3$ |
|---|---|---|---|---|---|---|---|---|---|---|
| A | 10.3 | 156 | DETA | Thermal | 235 | <1 | <1 | 225 | 81.8 | 83.8 |
| B | 10.6 | 165 | TETA | Thermal | 235 | <1 | 2.5 | 227 | 81.5 | 83.4 |
| C | 7.7 | 43 | DETA | Liq. CH$_2$O | 275 | 9 | 28 | 245 | 78.5 | 80.0 |
| D | 7.5 | 45 | TETA | Liq. CH$_2$O | 275 | 12 | 22 | 239 | 80.2 | 81.8 |
| E | 8.4 | 67 | TETA | Gas CH$_2$O | 260 | 10 | 43 | 235 | 81.3 | 82.4 |
| F | 7.9 | 51 | DETA | Thermal | 235 | <1 | 1.3 | 236 | 79.5 | 80.6 |
| G | 8.4 | 67 | | Oven heated 260° C./43 hrs. | 260 | 6 | 20 | 241 | 80.0 | 81.2 |
| The following catalysts were tested as whole particles - those above were crushed after preparation and sieved to 30–40 mesh before testing. | | | | | | | | | | |
| H | 7.9 | 51 | DETA | Thermal | 235 | <1 | 1.2 | 234 | 77.8 | 79.3 |
| I | 7.5 | 45 | TETA | Liq. CH$_2$O | 275 | 16 | 28 | 275* | 42.6 | 43.3 |

*The EO concentration was only 1.78 mol % in reactor effluent - 275° C. was maximum operating temperature of our equipment.

EXAMPLE XI

A series of EO catalysts and reactor tests were conducted on these catalysts under two different sets of oxygen process conditions. The purpose of these tests was to demonstrate the unique performance of my catalyst for improved selectivity and oxide production. The amines used to prepare the silver catalysts are listed below:
A. ethylenediamine
B. 1,2-propanediamine
C. 1,3-propanediamine
D. 2-methyl-1,2-propanediamine
E. diethylenetriamine The vicinal diamines of butane were not examined because these compounds were neither readily available nor readily prepared. Furthermore, the performance trend we observed in going from ethylenediamine to propylenediamines will show that the longer the carbon chain length, the poorer the diamine from a catalyst development standpoint. The latter amine (E) listed above is used in the manufacture of our novel catalyst and is quite different in structure and reactivity from the vicinal diamines A, B, and D and from the 1,3-diamine (C).

All of the catalysts were prepared using the same manufacturing procedure, with the amount of amine used based on approximately six amine equivalents per gram-atom of silver in the silver carboxylate-amine complex. The amino group/silver ratio was sufficiently high to form the desired complex and to allow excess amine for solubility improvement. The maximum amount of amine used, however, is not critical since the quantity must ordinarily be just sufficient to dissolve the amount of silver carboxylate necessary to give the desired silver metal concentration on the catalyst support. Any excess amine is simply "burned off" or volatilized during the high temperature catalyst activation step in a forced-air oven, normally at 250°-260° C. for one hour. This procedure immediately follows the drying step and leads to the finished catalyst. In each catalyst preparation, the aqueous silver carboxylate-amine complex solution was impregnated on a controlled pore size, low surface area, spherical α-alumina support designated as Norton LSA-05588. All of the catalysts described above contained 6.2±0.3 wt % silver and 142±7 ppm by weight of cesium as metal. These concentrations were prepared within the lower limits of analytical accuracy of an atomic absorption spectrophotometer operating in the flame emission mode.

An obvious difference in the physical appearance of the catalyst samples was apparent after the final manufacturing step was completed. Our catalyst based on diethylenetriamine was a uniform gray color in appearance with a brown hue, whereas the others (A, B, C, D) were mottled silver-white and gray in appearance with a brown hue in the gray portion.

The catalysts were tested using a small scale reactor very similar to that described in prior art. The catalyst weight was 3.5 g (~4.4 cc) and the reactor feed consisted of ~30 mol % ethylene, 30 mol % methane, 8 mol % oxygen and balance nitrogen, along with 4-5 ppm ethylene dichloride moderator. The reactor pressure was 200 psig and the reactor feed rates were the same for all catalysts tested. The rates were established along with moderator concentration to give reactor operating temperatures in the range specified in prior art. The catalysts were tested under conditions which would give a fixed EO concentration of 1.85 mol % in the reactor outlet, and those which would give a constant oxygen conversion of 52 mol %, the same test as described in prior art. The catalyst test sequence was D-E-A-B-C-E. Our catalyst (E) was retested at the end of the sequence to demonstrate the reproducibility and accuracy of our reactor and analytical system. A summary of these results is shown below:

| OXYGEN PROCESS DATA | | | | |
|---|---|---|---|---|
| | At EO conc. of 1.85 mol % | | | |
| Catalyst No. | Reactor temp, °C. | $S_3$, mol % | $S_2$, mol % | $O_2$ conv. mol % |
| A | 240 | 83.4 | 80.3 | 25.9 |
| B | 251 | 81.5 | 78.5 | 27.7 |
| C | 253 | 80.2 | 77.3 | 29.0 |
| D | 251 | 80.0 | 77.4 | 28.9 |
| E | 236 | 84.1 | 81.7 | 25.2 |
| E (repeat) | 237 | 84.3 | 81.6 | 24.8 |
| | At constant $O_2$ conv. of 52 mol % | | | |
| Catalyst No. | Reactor temp, °C. | $S_3$, mol % | $S_2$, mol % | EO outlet conc., mol % |
| A | 260 | 78.0 | 77.0 | 3.06 |
| B | 265 | 77.1 | 74.9 | 2.95 |
| C | 269 | 75.5 | 73.0 | 2.76 |
| D | 268 | 75.0 | 73.2 | 2.76 |
| E | 257 | 80.9 | 78.7 | 3.36 |
| E (repeat) | 259 | 81.2 | 78.7 | 3.42 |

As the performance calculations indicate, my catalyst prepared from a silver complex with diethylenetriamine was clearly superior in all performance categories to the prior art catalysts described above.

EXAMPLE XII

Preparation of Catalysts

A large batch of silver oxalate was prepared as follows: A hot solution of 454 g of A.R. silver nitrate dissolved in 1000 cc deionized water (di $H_2O$) was added slowly to a hot, stirred solution of 199 g of A.R. ammonium oxalate in 1000 cc di $H_2O$. The solution was stirred for 15-20 min., solids were allowed to settle, then supernatant liquid was decanted. Then 1000 cc di $H_2O$ was added, the solution was stirred, and solution was allowed to stand overnight. The silver oxalate was washed again with 1000 cc di $H_2O$, then filtered on a Buchner funnel under aspirator vacuum to a dripdry state. The silver oxalate was weighed and divided into four equal parts (440 g÷4=110 g). The volume of 110 g of diethylenetriamine (DETA) was measured (115 cc) and the same volumes of ethylenediamine (EDA) and triethylenetetramine (TETA) were used in the following experiments. The TETA was a highly-purified fraction containing predominantely the linear isomers; commercial TETA was demonstrated earlier to be unsatisfactory for making silver catalyst. For each catalyst, the appropriate amine was added to a slurry of 110 g of silver oxalate in 113 g of di $H_2O$ with stirring, keeping the solution temp. below 40° C. When all solids were dissolved, four promoter solutions were prepared as indicated below:

A. promotor soln. prepared from 0.25 g of 50% aqueous CsOH soln. in 13 g di $H_2O$.
B. promoter soln. prepared as in A.
C. promoter soln. prepared as in A.
D. promoter soln. prepared from 0.25 g of 50% aqueous CsOH soln. and 1.32 g of $HClO_4$ soln. (from 20 g of 71% $HClO_4$ in 94 g di $H_2O$) in 12 g di $H_2O$.

After one of the promoter solns. above was added to each of the four silver solutions, Norton 05588 ¼" ring support was added to the finished solutions. Enough support was added to each solution so all was immersed. The supports and solutions were placed in a vacuum dessicator and a pump vacuum of 10-25 mm Hg was pulled for five minutes. The vacuum was broken and the soln. was allowed to absorb into support for one min. Then, the wet supports were placed in a stainless steel basket inside a reaction kettle, one at a time, and subjected to pump vacuum (10-25 mm) for three min., then to reduce vacuum with air bleed for three min. The purpose here was to remove the adhering solution film from the support surface. The four batches of impregnated support, now appearing dry on the surface, were transferred to a compartmented ½"×18"×20" stainless steel wire basket. Inert support was added to fill the compartments. The wire basket was then mounted vertically in a forced air oven preheated to 125°-130° C., then heated at this temp for one hour with one-pass air flow at 5–10 ft³/min. The oven temp was raised to 255°–260° over 15 min. then held at this temp for one hour with 75% air recirculation. At the end of this period, the catalyst was cooled and weighed. The finished catalyst weight, appearance and silver/cesium concentrations are shown below:

| Catalyst No. | Amine used | Wt. catalyst | Appearance | Wt % Ag | ppm Cs |
|---|---|---|---|---|---|
| A | DETA | 263 g | Charcoal gray, uniform color throughout | 9.7 | 146 |
| B | EDA | 296 g | Mottled surface, gray exterior, off-yellow interior | 9.5 | 142 |
| C | TETA | 280 g | Same as for -59B | 9.8 | 144 |

Testing of Catalysts

Each of the above catalysts was ground and sieved to 30–40 mesh, then 3.5 g was loaded in a 0.20×20″ stainless steel reactor tube and tested under nitrogen ballast, oxygen process conditions—as shown below:

| Feed composition, mol % | | Conditions | |
|---|---|---|---|
| Oxygen | 7 | Feed rate: | 250 sccm |
| Ethylene | 17 | Pressure: | 200 psig |
| Carbon dioxide | 11 | Startup temp: | 250° C. |
| Nitrogen | balance | EDC inhibitor: | 0.5 ppm |

The four catalysts are compared below under three sets of conditions: constant operating temp (250° C.), constant oxygen conversion (52 mol %), and constant EO production (2.0 mol %).

| Catalyst No. | Operating temp, °C. | Oxygen conv., mol % | EO production mol % | $S_2$ mol % | $S_3$ mol % |
|---|---|---|---|---|---|
| 5347-59A | 250 | 27 | 1.9 | 80.1 | 86.5 |
| -59B | 250 | 31 | 1.9 | 78.0 | 83.8 |
| -59C | 250 | 37 | 2.3 | 76.8 | 83.6 |
| -59A | 262 | 52 | 3.3 | 77.8 | 84.4 |
| -59B | 262 | 52 | 3.0 | 75.5 | 81.3 |
| -59C | 258 | 52 | 2.8 | 74.2 | 81.0 |
| -59A | 250 | 28 | 2.0 | 80.2 | 86.4 |
| -59B | 250 | 31 | 2.0 | 78.0 | 83.8 |
| -59C | 247 | 32 | 2.0 | 77.6 | 84.0 |

These data clearly show that silver catalyst made with diethylenetriamine (DETA) is superior to those made with ethylenediamine (EDA) and triethylenetetramine (TETA).

I claim:

1. An improved method for epoxidizing ethylene to ethylene oxide in the vapor phase, which comprises the step of intimately contacting ethylene with a molecular oxygen-containing epoxidizing agent in the presence of a cesium-modified, supported silver catalyst at epoxidizing temperatures from about 200° C. to about 300° C., wherein the catalyst is prepared by contacting a porous, inorganic, catalyst support material with an impregnating solution; and, heating the impregnated support material at temperatures from about 50° C. to 300° C. to evaporate volatiles and activate said catalyst, wherein said impregnating solution comprises an effective amount of a cesium salt in solution with a silver carboxylate/amine complex of a silver carboxylate dissolved in a solubilizing amount of an amine-containing complexing agent comprising diethylenetriamine.

2. The method of claim 1 wherein the said ethylene is contacted with a molecular oxygen-containing epoxidizing agent in the presence of the said supported, cesium-modified silver catalyst and in the presence of an effective amount of at least one inhibitor to retard the combustion of ethylene to carbon dioxide.

3. The method of claim 1 wherein the said ethylene is contacted with a molecular oxygen-containing epoxidizing agent in the presence of said supported, cesium-modified, silver catalyst and in the presence of an effective amount of ethylene dichloride to retard combustion of ethylene to carbon dioxide.

4. The method of claim 1 wherein the said cesium salt is cesium hydroxide.

5. The method of claim 1 wherein the said silver carboxylate is selected from the silver salts of monocarboxylic acids, dicarboxylic acids and mixtures thereof.

6. The method of claim 1 wherein the said silver carboxylate is silver oxalate.

7. The method of claim 1 wherein the silver carboxylate is silver oxalate, said complexing agent is diethylenetriamine, and said cesium salt is cesium hydroxide.

8. An improved method for epoxidizing ethylene to ethylene oxide in the vapor phase, which comprises the step of intimately contacting ethylene with a molecular oxygen-containing epoxidizing agent in the presence of a cesium-modified, supported silver catalyst at epoxidizing temperatures from about 200° C. to about 300° C., wherein the catalyst is prepared by contacting a porous, inorganic catalyst support material with an impregnating solution comprising a solvent, an effective amount of a cesium salt and a silver carboxylate/amine complex; and heating the impregnated support material at temperatures from about 50° C. to 300° C. to evaporate volatiles, decompose said complex and activate said catalyst, wherein said silver carboxylate/amine complex comprises a silver carboxylate dissolved in a solubilizing amount of an amine-containing complexing agent comprising diethylenetriamine.

9. The method of claim 8 wherein the said solvent is water.

10. An improved method for epoxidizing ethylene to ethylene oxide in the vapor phase, which comprises the step of intimately contacting ethylene with a molecular oxygen-containing epoxidizing agent in the presence of a cesium-modified, supported silver catalyst at epoxidizing temperatures from about 200° C. to about 300° C., wherein the catalyst is prepared by contacting a porous, inorganic, catalyst support material with an impregnating solution; comprising an effective amount of a cesium salt dispersed in a silver carboxylate-amine complex of a silver carboxylate dissolved in a solubilizing amount of an amine-containing complexing agent comprising diethylenetriamine; drying said support at temperatures from about 50° C. to 150° C. to evaporate volatiles; and heating the dried support material at temperatures from about 200° C. to 300° C. to decompose said complex and activate said catalyst.

11. The method of claim 10 wherein said silver carboxylate-amine complex is prepared by dissolving the silver carboxylate in a solubilizing amount of said amine complexing agent at temperatures of from 0° C. to 50° C.

12. The process of claim 10 wherein said impregnating solution further contains water.

13. The method of claim 10 wherein said contacting is accomplished by immersing said support material in said impregnating solution at temperatures of about 0° C. to 50° C. and atmospheric pressure; and evacuating the immersed support material at pressure of from about 1 to about 2 mm/Hg and temperatures of 20° C. to 40° C. to remove entrapped air.

14. The method of claim 10 wherein said silver carboxylate is silver oxalate, wherein said complexing agent is diethylenetriamine and wherein said cesium salt is cesium hydroxide.

15. The method of claim 10 wherein said support material is a high purity α-alumina material having an average pore diameter of from about 3 to about 7μ with a pore volume of from about 0.3 to about 0.6 cc/g and a surface area less than about 1 m²/g.

* * * * *